(12) United States Patent
Reuter

(10) Patent No.: US 6,570,036 B1
(45) Date of Patent: May 27, 2003

(54) CO-CRYSTALLIZATION PROCESS

(75) Inventor: Karl Reuter, Freiburg (DE)

(73) Assignee: Reuter Chemische Apparatebau KG [DE/DE], Freiburg (DE)

(*) Notice: Subject to any disclaimer, the term of this patent is extended or adjusted under 35 U.S.C. 154(b) by 0 days.

(21) Appl. No.: 09/914,642

(22) PCT Filed: Mar. 3, 2000

(86) PCT No.: PCT/EP00/01858
§ 371 (c)(1),
(2), (4) Date: Aug. 31, 2001

(87) PCT Pub. No.: WO00/53283
PCT Pub. Date: Sep. 14, 2000

(30) Foreign Application Priority Data

Mar. 5, 1999 (EP) .............................. 99200648

(51) Int. Cl.⁷ .................. B01D 9/00; C07C 309/00; C07B 57/00
(52) U.S. Cl. ..................... 562/30; 23/300; 564/304
(58) Field of Search ................ 562/30; 564/304; 23/296, 300

(56) References Cited

U.S. PATENT DOCUMENTS 5,898,075 A    4/1999  McCague et al.
6,235,927 B1 *  5/2001  Vries et al. ............... 562/401

FOREIGN PATENT DOCUMENTS

| EP | 0 548 028 A | 6/1993 |
| EP | 0 838 448 A | 4/1998 |
| GB | 865 311 A | 4/1961 |
| WO | WO 97/32644 A1 | 9/1997 |

OTHER PUBLICATIONS

The Merck Index, 9ᵗʰ ed., Merck & Co. p. 220 (1976).*
Jean Jacques et al, *Enantiomers, Racemates, and Resolutions*, "Dissociable Compounds and Complexes", John Wiley & Sons, New York, NY USA (1981), XP002115263, pp. 307–317.

* cited by examiner

Primary Examiner—John M. Ford
Assistant Examiner—Zachary C. Tucker

(57) ABSTRACT

A process for isolating one or more enantiomer components from a mixture of enantiomers through co-crystallization is disclosed.

17 Claims, No Drawings

CO-CRYSTALLIZATION PROCESS

This is a U.S. National Stage Application, filed under 35 U.S.C. 371, of PCT/EP00/01858, which was filed Mar. 3, 2000.

BACKGROUND OF THE INVENTION

The present invention relates to a process for isolating enantiomer components from a mixture of enantiomers, as well as to separating a racemate into its enantiomeric components. Separated, single enantiomers are extremely important in certain fields of use, since they contain desired properties whereas their enantiomer pair may contain undesirable properties.

Isolation of enantiomers from a mixture of enantiomers is typically difficult because the enantiomers generally have identical physical properties, such as melting and boiling points, or other such properties typically used for separation. Moreover they tend to crystallize as racemic crystals rather than as a conglomerate consisting of a mixture of pure enantiomer crystals which would be separable by preferential crystallization. Thus, a common way today to obtain enantiomers is not through isolating individual enantiomers from a mixture, but rather through asymmetric synthesis of the enantiomer.

Techniques for isolating enantiomers in use today include various embodiments of chromatography, such as simulated moving bed chromatography (SMB). Chromatography-based methods, however, to date are not capable of isolating some enantiomers and/or cannot isolate some enantiomers economically in commercial quantities.

Various crystallization methods have also been proposed for separating enantiomers from a mixture, including preferential crystallization, co-crystallization and emulsion-crystallization. C.f. EP 0 548 028 A1; WO 97/32644; EP 0 838 448 A1; U.S. Pat. No. 5,898,075. While these methods overcome many of the shortcomings in crystallization, they also have some shortcomings. Preferential crystallization works only with racemates forming conglomerates. Furthermore, it is difficult to conduct with many conglomerates, since the systems tolerate only a small degree of super-saturation before spontaneous nucleation of the unwanted isomer occurs.

In co-crystallization, the yields of the enantiomer to be isolated and its co-crystallization agent are often poor (<95%), and it is normally difficult to recover the other enantiomer of the mixture in pure form. Furthermore, it can be difficult to identify a suitable co-crystallization agent that is inexpensive and readily accessible, and which enables crystallization of the desired enantiomer in high yield. Through emulsion crystallization some racemates forming racemic crystals (i.e. conglomerates and especially racemic compounds; see R. A. Sheldon, *Chirotechnology,* Marcel Dekker, Inc. 1993 (p. 174) for general definitions of terminology) can be separated, however the majority of the racemic crystals forming racemates cannot be separated even by normal emulsion crystallization.

It has now been found that the aforementioned problem can be avoided through the use of two co-crystallization agents which selectively form co-crystals with the (R) and (S) enantiomers of a mixture of enantiomers. The co-crystals so-formed can then be readily isolated and subsequently treated to yield the desired enantiomers.

In a second aspect of the invention, one or more enantiomers can be isolated from a mixture of enantiomers through co-crystallization from an emulsion. Use of an emulsion lends additional benefits characteristic of emulsion crystallization to the present invention.

SUMMARY OF THE INVENTION

The present invention provides a process for isolating enantiomer components from a mixture of enantiomers through co-crystallization comprising the steps of (a) forming a solution comprising the mixture of enantiomers (R) and (S) and co-crystallization agents $C_1$ and $C_2$, wherein $C_1$ and $C_2$ are chiral or achiral, with the proviso that at least one of $C_1$ and $C_2$ is chiral and $C_1$ and $C_2$ do not form an enantiomeric pair, whereby $C_1$ forms a co-crystal with (R) and $C_2$ forms a co-crystal with (S); (b) super-saturating the solution in $C_{1*}(R)$ and $C_{2*}(S)$; (c) inducing crystallization of co-crystals of $C_{1*}(R)$ and $C_{2*}(S)$; and (d) isolating the $C_{1*}(R)$ co-crystals and $C_{2*}(S)$ co-crystals.

A second aspect of the present invention provides a process for isolating one or more enantiomers from a mixture of enantiomers through co-crystallization from an emulsion comprising the steps of (a) forming an emulsion of organic liquid droplets in a continuous water phase, which emulsion contains the mixture of enantiomers and a co-crystallization agent for each enantiomer to be isolated, wherein the co-crystallization agents are chiral or achiral, with the proviso that at least one co-crystallization agent is chiral, whereby the co-crystallization agent forms a co-crystal with its corresponding enantiomer; (b) super-saturating the emulsion in (co-crystallization agent) $_*$(enantiomer); (c) inducing crystallization of co-crystals of (co-crystallization agent) $_*$(enantiomer), whereby crystallization takes place in the water phase; and (d) isolating the co-crystals of (co-crystallization agent) $_*$(enantiomer).

DETAILED DESCRIPTION OF THE INVENTION

Crystallization processes are known and need not be described in detail here. Their basic premise is that a solution is formed containing the desired substance, the solution is supersaturated by conventional techniques such as cooling of the solution, and then crystallization of the desired substance is induced, either spontaneously or by seeding with seed crystals of the desired substance. The present extends this technology through the judicious choice of co-crystallization agents which will form co-crystals with the enantiomers of a mixture of enantiomers. The solution accordingly contains the enantiomers and the co-crystallization agents, is super-saturated, and then crystallization of co-crystals of the enantiomers and co-crystallization agents is induced.

Co-crystals of the co-crystallization agents and the enantiomers are indicated in the present invention according to the convention '(co-crystallization agent) $_*$(enantiomer)'. In a typical embodiment of the invention, two co-crystallization agents, $C_1$ and $C_2$, will be employed. They will, accordingly, selectively form co-crystals with the (R) and (S) enantiomers of the mixture of enantiomers, as indicated by '$C_{1*}(R)$' and '$C_{2*}(S)$'. All stoichiometries are intended to be covered with this nomenclature, i.e., '$C_{1*}(R)$' should be understood to include 1 $C_{1*}(R)$; 2 $C_{1*}(R)$; 1 $C_{1*2}(R)$; 2 $C_{1*}3(R)$; etc.

(R) and (S) may be present in the enantiomeric mixture in any ratio, including a 50/50 ratio, i.e. as a racemate. The mixture may comprise more than one pair of (R) and (S) enantiomers. The enantiomers can be bases in which case the co-crystallization agents typically will be acids. Or, the enantiomers can be acids in which case the co-crystallization agents typically will be bases. Bases will typically be amines. Alternatively, the enantiomers and/or co-crystallization agents can be neutral co-crystal-forming compounds.

The enantiomers can be pharmaceutical or agrochemical substances, fragrances, food additives, chemical intermediates or the like.

Co-crystallization agents are compounds that selectively form co-crystals with the (R) and (S) enantiomers. Co-crystallization agents may be either chiral or achiral, though at least one of them must be chiral. Preferably, both are chiral. Co-crystallization agents can not form an enantiomeric pair as this could lead to formation of a racemic co-crystal consisting of $C_{1*}C_{2*}R_*S$.

An exception to the limitations on the co-crystallization agents applies to the case of co-crystallization from an emulsion (later described). In this case, the process of the present invention can be carried out using one co-crystallization agent to isolate a single enantiomer (R) or (S) from the mixture of enantiomers. The co-crystallization agent must be chiral. Where two co-crystallization agents are used to isolate both enantiomers, the co-crystallization agents can be chiral or achiral, with the proviso that at least one is chiral. In the case both are chiral they can form an enantiomeric pair. Typically, however, the conditions of the previous paragraph will also apply to emulsion crystallization.

The co-crystallization agents used in the present invention are preferably chosen according to the following guidelines:

Co-crystals $C_{1*}(R)$ and $C_{2*}(S)$ should be less soluble than all other crystals that may form (e.g. $C_{1*}(R)_*(S)$; $(R)_*(S)$; $C_{1*}C_{2*}(R)_*(S)$; etc), under the conditions at which crystallization takes place. In the case of emulsion crystallization, however, their solubilities can be somewhat higher than those of other crystals, since control over what crystallizes is possible through seeding with the desired co-crystal (see also further discussion on emulsion crystallization);

Concentrations of the co-crystallization agents and crystallization conditions are selected such that $C_{1*}(R)$ and $C_{2*}(S)$ can either be 1) alternately co-crystallized according to preferential crystallization: or (especially in the case of emulsion crystallization) 2) simultaneously crystallized, when differences in crystal size or shape between $C_{1*}(R)$ and $C_{2*}(S)$ allow separation by sieving or sedimentation;

At least one of the co-crystallization agents is chiral.

In addition, $C_1$ and $C_2$ may each comprise a family of two or more co-crystallization agents. Each member of the family typically have a common base structure. The features defined above for $C_1$ and $C_2$ will apply to each member of the family.

Inducing crystallization (step (c)) can be carried out either by seeding with co-crystals of (co-crystallization agent)$_*$ (enantiomer) (i.e. $C_{1*}(R)$, $C_{2*}(S)$ etc.) or can occur without seeding (i.e. by spontaneous crystallization). Seeding can be carried out consecutively or (especially in the case of emulsion crystallization) simultaneously. In the case of consecutive seeding, the solution is first seeded with co-crystals of $C_{1*}(R)$ to induce crystallization of $C_{1*}(R)$ co-crystals, which co-crystals are then isolated from solution, and then the solution is seeded with co-crystals of $C_{2*}(S)$ to induce crystallization of $C_{2*}(S)$ co-crystals, which co-crystals are then isolated from solution. Or, this order of seeding can be reversed.

In the case of simultaneous seeding, differences in crystal size or shape between $C_{1*}(R)$ and $C_{2*}(S)$ allow their separation by sieving or sedimentation.

Prior to seeding, it is desirable that the super-saturated solution (or emulsion) contains no seed crystals of substances apart from those that are intended to be seeded. Any seeds present can be dissolved by ultrasound or heating, with such dissolving of seeds hereinafter referred to as "homogenisation".

In a preferred embodiment of the invention, significant improvements in yields can be obtained if the crystallization process of the present invention is carried out with recycle of solution (or emulsion). This necessitates, in effect, that the solution (or emulsion) is replenished with the mixture of enantiomers and co-crystallization agents and then steps (a)–(d) are repeated. The order in which replenishing with the mixture of enantiomers and co-crystallization agents and steps (a)–(d) are repeated can vary. The mixture of enantiomers and co-crystallization agents can be replenished together, in a single step, following step (d). Or, the mixture of enantiomers and co-crystallization agents can be replenished after isolation of $C_{1*}(R)$ co-crystals and again after isolation of $C_{2*}(S)$ co-crystals. Other sequences are possible, as will be known to one skilled in the art.

Recycle can be applied to a variation of the second aspect of the present invention which brings about particular advantages. In this variation, both enantiomers are isolated from the mixture using two separate emulsions: a first emulsion is formed for super-saturating, inducing crystallization and isolating co-crystals of the first enantiomer and a second emulsion is formed for super-saturating, inducing crystallization and isolating co-crystals of the second enantiomer in steps (b), (c) and (d) of the process. Then, following isolation of co-crystals in step (d), a further step (e) is employed wherein the left-over first emulsion is recycled for use as the second emulsion and the left-over second emulsion is recycled for use as the first emulsion in step (a).

By carrying out a recycle, several advantages are obtained. The co-crystallization agents, which are often costly, can be re-used. The process can be carried out continuously. Yield of co-crystal after each crystallization step need not be as high as is required in classical (non-emulsion) co-crystallization (where only one enantiomer is recovered by co-crystallization with a chiral co-crystallization agent), whereas overall yield with recycle can be significantly higher. This enables the use of a variety of co-crystallization agents in the present invention, which in turn enables a wide range of mixtures of enantiomers to be resolved economically. Also, the present process isolates both enantiomers, whereas classical co-crystallization only one. The 'other' enantiomer can have value as an intermediate, as a co-crystallization agent for another separation process or to racemize it into the 'desired' enantiomer in a separate step. Racemization in the crystallization solution is an often employed process. However, the racemization conditions are restricted to those possible in the given crystallization solvent, in the presence of the desired enantiomer and its co-crystallization agent, and the like.

The desired enantiomer can be isolated from the co-crystallization agent using standard techniques, such as extraction of a co-crystallizing acid by an alkaline solution or vice versa.

Particular advantages are gained if the crystallization is carried out from an emulsion. Emulsions allow, for example, crystallization at constant, low temperature with little or no spontaneous nucleation, extreme super-saturation, slow crystal growth, very regular crystal shapes, narrow distribution of crystal size and high purities.

Emulsions also facilitate the possibility of simultaneous seeding of co-crystals. Accordingly, the solution can be (in a preferred embodiment is) seeded in step (c) simultaneously with seed co-crystals of $C_{1*}(R)$ and $C_{2*}(S)$, and the isolation of step (d) is carried out by separating co-crystals of $C_{1*}(R)$ from co-crystals of $C_{2*}(S)$ by sieving or sedimentation Emulsion crystallization can be used to isolate one or more enantiomers from the mixture of enantioners.

Emulsions are, by definition, "droplets" dispersed in a "continuous phase". In the present invention, the droplets are organic liquid droplets and the continuous phase is a water phase. The emulsion optionally contains additives such as surfactants and dispersants, known in the art, for assisting formation and stabilization of the emulsion, and for facilitating the transport of the co-crystallization agent and/or enantiomer out of the organic liquid droplets and into the water phase, where crystallization takes place on a crystal surface (i.e. either the seed crystal or spontaneously formed crystal). Such surfactants and/or dispersants will be chosen according to the nature of the emulsion, and can be nonionic, anionic and/or cationic. The surface active agent will normally be present in an amount of 0.01–30 w/w %, preferably 0.1–20 w/w %.

The droplets typically vary in diameter from approximately 0.05 to 80 μm. Droplets with diameter in the range of 0.3 to 80 μm are known as "macrodroplets", and the emulsions as "macroemulsions". Droplets with diameter in the range of 0.05 to 0.3 μm are known as "microdroplets", and the emulsions as "microemulsions". For the sake of simplicity, the terms "droplets" and "emulsions" as used herein also encompass both macro- and microdroplets and macro- and microemulsions.

The organic liquid phase of the droplet will be water insoluble. 'Water insoluble' in this context means anything less than water miscible, though in most cases the organic liquid phase will mix with water in an amount not more than 30% w/w at the temperature at which crystallisation takes place.

In the emulsion of the present invention, at least one of the co-crystallization agents or enantiomers will be present primarily in the organic liquid droplets of the emulsion. 'Primarily' means in this sense its concentration in the organic liquid droplets is at least 20% higher than in the water phase (the relative solubility can e.g. be determined at least approximately in the absence of the tenside, determining the equilibrium distribution).

The water may further contain a buffering agent, such as sodium acetate and acetic acid, for maintaining pH of the emulsion at a desired level, antifreezing agents and solubility adjusting agents, as is known in the art.

Emulsions according to the invention can be formed using techniques known in the art. A suitable example for carrying out the invention, which is not intended to limit the cope of the present invention in any way, is as follows (Synperonic NP10 is a nonlyphenol surfactant, ethoxylated with 10 mol ethyleneoxide, ICI PLC, England; Soprophor FL is a tristyrylphenol derivative, Rhodia, France):

EXAMPLE 1

Emulsion Crystallization with Consecutive Seeding 10.0 g of (±)-Camphor-10-sulfonic acid ((±)-CSA), 8.45 g Brucine and 7.0 g Chinidine are dissolved in 43 ml microemulsion made from 10% isobutanol, 30% DMF, 20% Synperonic NP 10 and 40% water. Heating to approx. 95–100° C. and cooling leads to a clear microemulsion.

Preparation of the seed crystals: 696.9 mg (+)-CSA and 1183.4 mg Brucine, and 696.9 mg (−)-CSA and 973.3 mg Chinidine are each dissolved in 5 ml of microemulsion made from isobutanol, Synperonic NP 10 and water, as described above. Crystallization takes place at room temperature over the course of several hours, yielding a suspension of co-crystals. The suspension is finely milled.

Seeding with the finely milled suspension of D-CSA*Brucine co-crystals results in crystal growth of D-CSA*Brucine co-crystals. After approximately thirty minutes the crystals are filtered off. In a second step the remaining microemulsion is homogenized and inoculated with a seed suspension of L-CSA*Chinidine co-crystals. After twenty minutes the precipitate of L-CSA*Chinidine is filtered off.

In order to recover the amines Brucine and Chinidine, a solution of NaOH in water (10%) is added to the salts of D-CSA*Brucine or L-CSA*Chinidine and extracted twice with $CH_2Cl_2$. The organic layer is dried over $MgSO_4$ and the solvent is evaporated under reduced pressure. The D- and L-CSA acids are recovered as the sodium salts in aqueous solutions.

EXAMPLE 2

Emulsion Crystallization with Consecutive Seeding

Racemic Naphthylethylamine (NEA) is separated into its enantiomeric components using the cocrystallisation agents S-Ibuprofen (Ibu) and (−)-Diacetone-ketogulonic acid (Ketgu).

The Composition of the microemulsion is:

10% Isobutanol

35% N-Methylpyrrolidinone (NMP)

10% Soprophor FL

45% Water

A mixture of racemic NEA (205.2 mg; 1.2 mmol) and S-Ibuprofen (123.6 mg; 0.6 mmol) is dissolved in 1.5 ml of a microemulsion (composition see above). Heating up the mixture to 95–100° C. and cooling down to room temperature leads to a clear supersaturated microemulsion. Seeding with a finely ground suspension of R-NEA*S-Ibuprofen crystals in water results in selective growth of the seed crystals. After 15 min. the crystals in the form of needles of R-NEA*S-Ibuprofen are filtered, washed with a little amount of water and dried.

(−)-Diacetone-ketogulonic acid (175.2 mg; 0.6 mmol) is added to the mother liquor from R-NEA*S-Ibuprofen crystallisation of the previous experiment. Heating up the mixture to 95–100° C. and cooling down to room temperature leads to a clear supersaturated microemulsion. Seeding with a finely ground suspension of S-NEA*(−)-Diacetone-ketogulonic acid crystals in water results in selective growth of the seed crystals. After 15 min. the crystals of S-NEA*(−)-Diacetone-ketogulonic acid in needle form are filtered, washed with a little amount of water and dried.

A mixture of racemic NEA (102.6 mg; 0.6 mmol) and S-Ibuprofen (61.8 mg; 0.3 mmol) is added to the 1.5 ml of mother liquor from S-NEA*(−)-Diacetone-ketogulonic acid crystallisation of the previous experiment. Heating up the mixture to 95–100° C. and cooling down to room temperature leads to a clear supersaturated microemulsion. Seeding with a finely ground suspension of R-NEA*S-Ibuprofen crystals in water results in selective growth of the seed crystals. After 15 min. the crystals of R-NEA*S-Ibuprofen in needle form are filtered, washed with a little amount of water and dried.

(−)-Diacetone-ketogulonic acid (87.6 mg; 0.3 mmol) is added to the mother liquor from R-NEA*S-Ibuprofen crystallisation of the previous experiment. Heating up the mixture to 95–100° C. and cooling down to room temperature leads to a clear supersaturated microemulsion. Seeding with a finely ground suspension of S-NEA*(−)-Diacetone-ketogulonic acid crystals in water results in selective growth of the seed crystals. After 15 min. the crystals of S-NEA* (−)-Diacetone-ketogulonic acid in acid form are filtered, washed with a little amount of water and dried.

EXAMPLE 3

Emulsion Crystallization with Consecutive Seeding

2-Amino-1-butanol (ABL) is separated into its enantiomeric components using the co-crystallisation (−)-o,o'-dibenzoyl-tartaric acid and (−)-o,o'-ditolyl-tartaric acid.

The Composition of the microemulsion is:

10% Isobutanol

10% N-Methylpyrrolidinone (NMP)

10% Soprophor FL

70% Water

A mixture of racemic ABL (178.2 mg; 2 mmol) and (−)-o,o'-dibenzoyl-tartaric acid (358.4 mg; 1 mmol) is dissolved in 1 ml of a microemulsion (composition see above). Heating up the mixture to 95–100° C. and cooling down to room temperature leads to a clear supersaturated microemulsion. Seeding with a finely ground suspension of S-ABL* (−)-o,o'-dibenzoyl-tartaric acid crystals in water results in selective growth of the seed crystals. After 15 min. the crystals of S-ABL*(−)-o,o'-dibenzoyl-tartaric acid in the forms of rhomboidal plates are filtered, washed with a little amount of water and dried.

(−)-o,o'-ditolyl-tartaric acid (77.3 mg; 0.2 mmol) is added to the mother liquor from the S-ABL*(−)-o,o'-dibenzoyl-tartaric acid crystallisation of the above experiment. Heating up the mixture to 95–100° C. and cooling down to room temperature leads to a clear supersaturated microemulsion. Seeding with a finely ground suspension of R-ABL*(−)-o,o'-ditolyl-tartaric acid crystals in water results in selective growth of the seed crystals. After 15 min. the crystals of R-ABL*(−)-o,o'-ditolyl-tartaric in the form of bars are filtered, washed with a little amount of water and dried.

What is claimed is:

1. A process for isolating enantiomer components from a mixture of enantiomers through co-crystallization comprising the steps of
   (a) forming a solution comprising the mixture of enantiomers (R) and (S) and co-crystallization agents $C_1$ and $C_2$, wherein $C_1$ and $C_2$ are chiral or achiral, with the proviso that at least one of $C_1$ and $C_2$ is chiral and $C_1$ and $C_2$ do not form an enantiomeric pair, whereby $C_1$ forms a co-crystal with (R) and $C_2$ forms a co-crystal with (S);
   (b) super-saturating the solution in $C_{1*}(R)$ and $C_{2*}(S)$;
   (c) inducing crystallization of co-crystals of $C_{1*}(R)$ and $C_{2*}(S)$; and
   (d) isolating the $C_{1*}(R)$ co-crystals and $C_{2*}(S)$ co-crystals,
further comprising replenishing the solution with the mixture of enantiomers and co-crystallization agents and repeating steps (a)–(d).

2. A process according to claim 1 wherein the mixture of enantiomers is a racemate of (R) and (S) enantiomers.

3. A process according to claim 1 wherein both co-crystallization agents are chiral.

4. A process according to claim 1, wherein the enantiomers are bases and the co-crystallization agents are acids, or the enantiomers are acids and the co-crystallization agents are bases.

5. A process according to claim 4 wherein the bases are amines.

6. A process according to claim 1, wherein crystallization is induced in step (c) by seeding with co-crystals of $C_{1*}(R)$ and $C_{2*}(S)$.

7. A process according to claim 6 in which the solution is first seeded with co-crystals of $C_{1*}(R)$ to induce crystallization of $C_{1*}(R)$ co-crystals, which co-crystals are then isolated from solution, and then the solution is seeded with co-crystals of $C_{2*}(S)$ to induce crystallization of $C_{2*}(S)$ co-crystals, which co-crystals are then isolated from solution, or this order of seeding is reversed.

8. A process according to claim 6 wherein the co-crystals are simultaneously seeded.

9. A process according to claim 1 wherein the solution is the continuous water phase of an emulsion of organic liquid droplets in said continuous water phase, and crystallization takes place in the water phase.

10. A process according to claim 9 in which $C_{1*}(R)$ and $C_{2*}(S)$ co-crystals are seeded simultaneously in step (c) to induce crystallization of co-crystals of $C_{1*}(R)$ and $C_{2*}(S)$ and the isolation of step (d) is carried out by separating co-crystals of $C_{1*}(R)$ from co-crystals of $C_{2*}(S)$ by sieving or sedimentation.

11. A process according to claim 1, further comprising isolating the enantiomer from the co-crystallization agent.

12. A process for isolating both enantiomers from a mixture of enantiomers through co-crystallization from an emulsion comprising the steps of
   (a) forming an emulsion of organic liquid droplets in a continuous water phase, which emulsion contains the mixture of enantiomers and a co-crystallization agent for each enantiomer to be isolated, wherein the co-crystallization agents are chiral or achiral, with the proviso that at least one co-crystallization agent is chiral, whereby the co-crystallization agent forms a co-crystal with its corresponding enantiomer;
   (b) super-saturating the emulsion in (co-crystallization)$_*$ (enantiomer);
   (c) inducing crystallization of co-crystals of (co-crystallization agent)$_*$(enantiomer), whereby crystallization takes place in the water phase; and
   (d) isolating the co-crystals of (co-crystallization agent)$_*$ (enantiomer).

13. The process of claim 12 wherein at least one of the co-crystallization agents or enantiomers is present primarily in the organic liquid droplets of the emulsion.

14. A process according to claim 12 wherein the co-crystallization agents form an enantiomeric pair.

15. A process according to claim 12 for isolating both enantiomers from the mixture, wherein in step (a) a first emulsion is formed for super-saturating, inducing crystallization and isolating co-crystals of the first enantiomer and a second emulsion is formed for super-saturating, inducing crystallization and isolating co-crystals of the second enantiomer in steps (b), (c) and (d), and further comprising the step of
   (e) following isolation of co-crystals in step (d), recycling the left-over first emulsion for use as the second emulsion and the left-over second emulsion for use as the first emulsion in step (a).

16. A process according to claim 1, wherein the mixture is a mixture of the enantiomers of camphor-10-sulfonic acid or naphthylethylamine.

17. A process according to claim 16 wherein the mixture is racemic camphor-10-sulfonic acid or racemic naphthylethylamine.

* * * * *